United States Patent [19]

Killick

[11] 4,064,630
[45] Dec. 27, 1977

[54] DENTAL UNITS AND THE LIKE

[75] Inventor: Herbert Percy Killick, Blackpool, England

[73] Assignee: C.M.W. Laboratories Limited, London, England

[21] Appl. No.: 461,868

[22] Filed: Apr. 18, 1974

Related U.S. Application Data

[63] Continuation-in-part of Ser. No. 239,259, March 29, 1972, abandoned.

[30] Foreign Application Priority Data

| May 2, 1973 | United Kingdom | 20727/73 |
| May 2, 1973 | United Kingdom | 20728/73 |
| May 2, 1973 | United Kingdom | 20777/73 |
| July 18, 1973 | United Kingdom | 34250/73 |

[51] Int. Cl.² .......................................... A61C 19/00
[52] U.S. Cl. ................................................. 32/22
[58] Field of Search .......................................... 32/22

[56] References Cited

U.S. PATENT DOCUMENTS

| 3,638,310 | 10/1969 | Austin, Jr. | 32/22 |
| 3,771,226 | 11/1973 | Lieb et al. | 32/22 |
| 3,872,593 | 10/1965 | Thornton et al. | 32/22 |

Primary Examiner—Robert Peshock
Attorney, Agent, or Firm—Learman & McCulloch

[57] ABSTRACT

A dental unit has a manifold module incorporating respective fluid-conducting conduits for the supply of water and air to dental instruments, each conduit leading to a respective self-sealing coupling member, said members forming a set located on one outer face of the manifold module for simultaneous releasable connection to a set of respective mating members on a manifold extension module. The manifold module may be corrected directly or via one or more manifold extension modules to one or more instrument control modules. Alternatively, the manifold extension modules and/or instrument control modules may be connected directly to a set of self-sealing coupling members located on a set of conduits supplying water and air.

3 Claims, 4 Drawing Figures

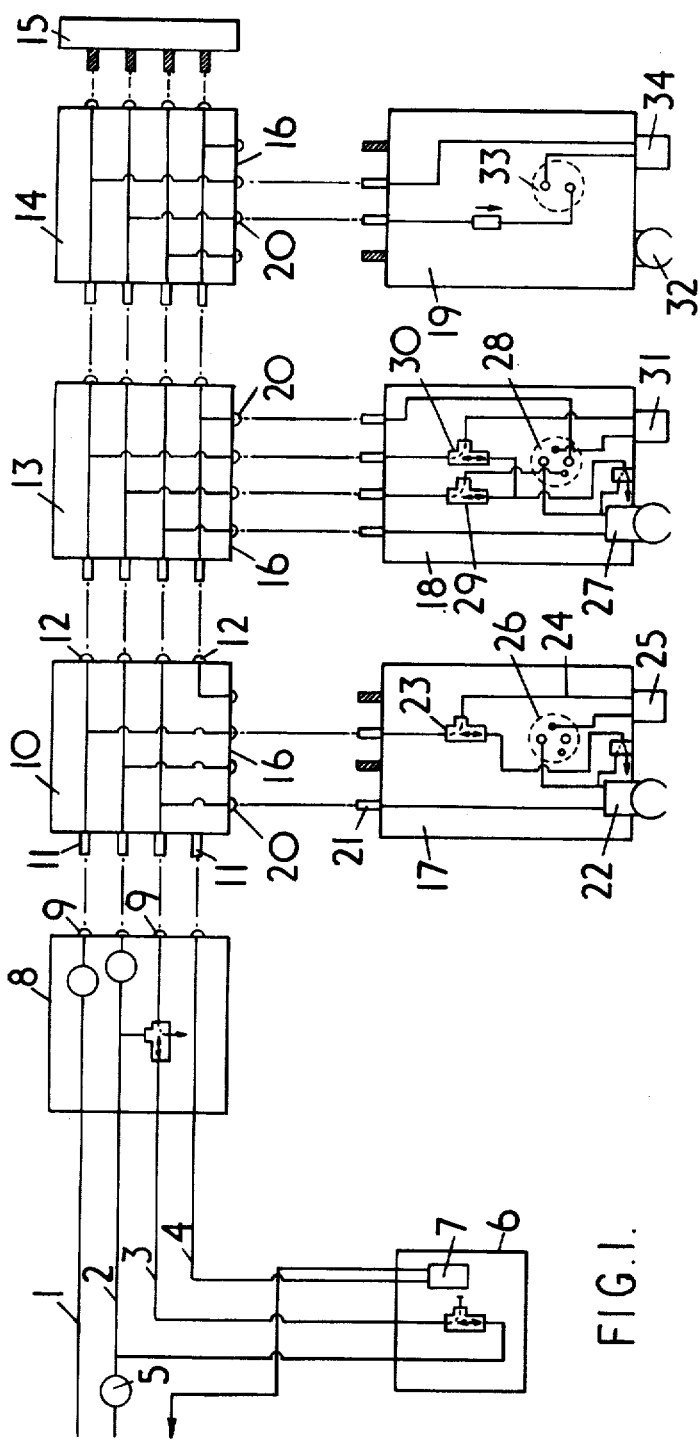
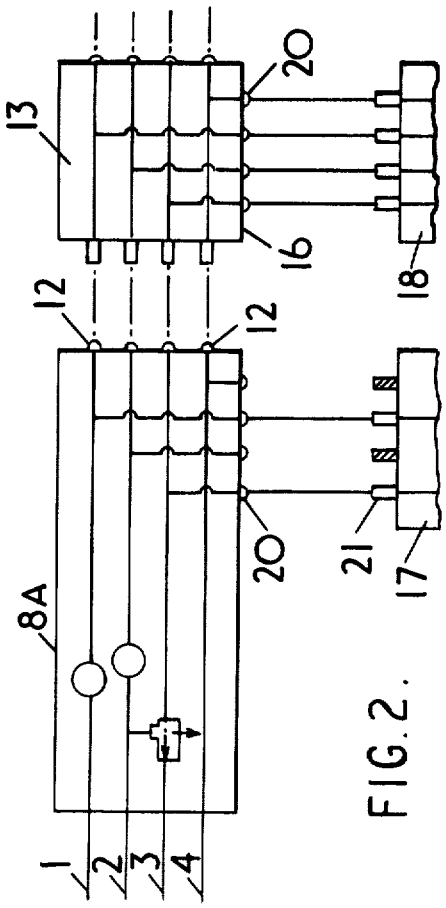
FIG. 1.
FIG. 2.

DENTAL UNITS AND THE LIKE

This Application is a continuation in part of Application Ser. No. 239,259 filed Mar. 29, 1972 and now abandoned.

This invention relates to dental units, which may be regarded as a centralised supply to which the various power and fluid consuming instruments employed by the dentist are connected.

Traditionally, such dental units have taken the form of a so-called console into which are built a number of valves and one or more power sources with connections to electricity, water and drainage and from which extend a spittoon and a dental instrument tray. Commonly, the various dental instruments are retractably housed under the tray and connected to the respective appropriate power and fluid sources in the body of the console. Depending on what facilities the dentist ordering the console unit requires, the appropriate instruments and supply connections in the console are provided by the manufacturer. To add further facilities at a later date is generally a matter requiring attention by an installation engineer. Other forms of dental units have been developed, including one in which a substantial part of the desired mobility is provided by having the centralised power connections in a casing which is itself mounted for swinging in the arc of a circle. In all these cases, however, the unit incorporates, as manufactured all the necessary power and fluid supply connections for the instruments ordered with the unit by the dentist and, in general, the attachment of further or different units requires the attention of a service engineer.

It is an object of the present invention to provide a construction of dental unit in which the instrument connections are of modular form, making it a simple matter for the dentist to extend, reduce or alter the instrumentation of his unit.

Another object is to facilitate the assembly and maintenance of dental units by the provision of a modular construction of the power and fluid distribution to the individual instruments whereby for example any faulty instrument control module can be exchanged for a new or factory conditioned unit without interruption for more than a few moments to the operability of the dental unit.

The present invention consists broadly in a dental unit comprising a manifold module incorporating respective fluid-conducting conduits for the supply of air and water to dental instruments, each conduit leading to a respective self-sealing coupling member, all said members forming a set located on one outer face of the manifold module for simultaneous releasable connection to a set of respective mating coupling members on a manifold extension module.

In a practical embodiment of the invention the unit will comprise a manifold module connected to a linking manifold extension module having said set of mating coupling members in one face thereof and at least one set of self-sealing coupling members in another face thereof, and respective fluid-conducting conduits leading from each of the said mating coupling members to one self-sealing coupling member in aid other face(s) said set(s) of self-sealing coupling members being arranged for simultaneous releasable connection to a set of respective mating coupling members on a further manifold extension module. In this practical embodiment the linking manifold extension module is preferably one having a pair of sets of self-sealing coupling members, i.e. preferably has a first set of self-sealing coupling members in a second face thereof and a second set of self-sealing coupling members in a third face thereof and respective fluid-conducting conduits leading from each of the said mating coupling members to one self-sealing coupling member in each of said second and third faces. The sets will generally comprise two or more such coupling members.

The dental unit may have further such linking manifold extension modules connected in series and the linking manifold extension module adjacent said manifold module may suitably be formed integral therewith.

In the simplest form of the invention, the units will provide a number of services (e.g. including water, air under pressure and exhaust) collated together in a manifold at an instrument storage area this manifold providing a succession of connections at which the individual manifold extensions for the various instruments may be plugged in so that the dentist when desiring an additional or a different instrument need only have the appropriate manifold extension module with the instrument. Conveniently, the manifold extension modules all have a similar pattern of connection members for establishing connection with the self-sealing orifice terminations of the manifold, some of these in appropriate cases being "blind" where the respective service is not required for the instrument in question. Generally, the extension module will incorporate an instrument carrier, which may be weight responsive to open a valve when the instrument is lifted off for use, and will generally also incorporate a control valve or valves for the individual instrument.

In a preferred embodiment of the invention, where (as will generally be the case) more than one instrument is to be employed, the manifold incorporates a connection for an extension joint, that is to say a module joint itself providing a connection for a manifold extension module as already described, and a connection for a further extension joint so that any number (within limits) of desired connections for manifold extension modules can be provided by plugging, in line, the appropriate number of modular extension joints. An end blank may also be provided for the last such joint.

Although two or three conduits have been referred to, it will be understood that more will generally be employed, in particular air at two different levels of pressure may be provided in respective conduits. Further electrical connections (preferably at low voltage) may be incorporated although the electrical connections may be provided separately if desired.

The individual instruments may be constructed with fixed connections to the respective manifold extension modules, or may be disconnectable therefrom so that they can readily be provided separately.

The manifold module will suitably be connected directly, or via one or more of the above linking manifold extension modules, to one or more instrument control manifold extension modules each incorporating controls for a respective dental instrument and appropriate fluid-conducting conduits leading from said mating coupling members to said dental instrument via said controls.

The dental unit of the invention will supply water and air under pressure and, via the manifold module, may supply air under two pressures although the module may be constructed to supply water and air at only one pressure, for example to supply a dental handpiece via an instrument control module.

The self-sealing coupling members employed in the dental units of the invention may conveniently be of the form described in copending application Ser. No. 23,826.

The manifold modules and extension modules of the apparatus of the invention take the form of modular blocks having a plurality of conduits running therethrough, and possibly passing through control valves, switches or the like. In addition each modular block has at least one set of coupling members adapted to co-operate with a corresponding set of coupling members in another modular block. The construction of such modular blocks is necessarily somewhat complex and it is an object of another embodiment of the present invention to provide a modular block which may be simply constructed.

Accordingly, the present invention consists in a dental unit of the sort described above wherein each module comprises a central block member having housings for at least one set of coupling members in one outer face thereof adapted to cooperate with a corresponding set of female or male coupling elements in another module, and housings for any valves or other controls for fluids passing through said module; an upper plate provided, in the surface thereof facing the central block, with a plurality of grooves; and a lower plate, provided in the surface thereof facing the central block, with a plurality of grooves, the grooves in the said plates being connected with the housings in the central block via holes in said central block to form the various conduits within the module.

The present invention also relates to a dental instrument control system in which dental instruments are supplied with the desired services (e.g. water, air and, optionally, exhaust) via instrument control modules similar to those described above, wherein the need for a dental unit provided with the above described manifold modules or linking extension manifold modules is obviated. Thus, in essence, the modification provides a system which does not employ the conventional concept of a centralised supply of services to all of a plurality of dental instruments. Broadly, in accordance with this invention, a set of canduits for supplying the necessary services to dental instruments are laid where desired, e.g. about a dental surgery or about a dental stand or chair, and are provided at suitable positions and intervals with sets of self-sealing coupling members connected to the respective fluid-conducting conduits, for simultaneous releasable connection to a set of respective mating coupling members on an instrument control module as defined above. If desired, two or more instrument control modules may be connected to the set of self-sealing coupling members via one or more linking extension modules as defined above. Alternatively, where it is desired to be able to attach more than one instrument to the service supply conduits at one place a plurality of the said sets of self-sealing couplings may be provided immediately adjacent to each other on the service supply conduits or the conduits may be directly connected to an integral member having two or more sets of the said self-sealing members thereon.

In its simplest form the system of the invention will generally provide for the provision of two services (namely compressed air and water) to the dental instrument although, of course, the system enables the provision of any number of such services and may, for example, provide air at two pressures, water and exhaust services in a manner similar to the dental unit described above.

The construction of the instrument control modules will be similar to that of the modules described above, the principal difference in the present system being that the modules are directly coupled with sets of coupling members directly attached to the service supply conduits. More particularly, the instrument control modules and/or linking modules (if any) are preferably constructed as described above, i.e. a central block member having housings for at least one set of coupling members in one outer face thereof adapted to cooperate with a corresponding set of female or male couplings elements in another module or on the supply system and housings for any valves or other controls for fluids passing through said module; an upper plate provided, in the surface thereof facing the central block, with a plurality of grooves; and a lower plate, provided in the surface thereof facing the central block, with a plurality of grooves; the grooves in the said plates being connected with the housings in the central block via holes in said central block to form the various conduits within the module.

As stated above, the set of conduits, which are generally arranged parallel to each other, may be run around a dental surgery and this form of installation is particularly useful when it is desired to supply the services to a plurality of dental chairs located in one surgery. Thus, in this case, the service supply conduits will be located within the surgery so as to provide convenient take-off points for the services for the various dental instruments at places close to the various chairs. Alternatively, or in addition, the set of service supply conduits may be arranged on the actual dental chair itself with one or more of the said sets of self-sealing couplings on the chair. This is a particularly useful system since the spatial relationship between the instrument control module and the patient is maintained constant, in contra-distinction to the prior art centralised dental unit systems.

The invention will be further described with reference to the accompanying drawings, in which:

FIG. 1 is a diagrammatic representation of a dental unit affording connections for three instruments in accordance with the invention;

FIG. 2 is a diagrammatic representation of a modification of the unit shown in FIG. 1 wherein units 8 and 10 are fixed integrally;

Figure 3:
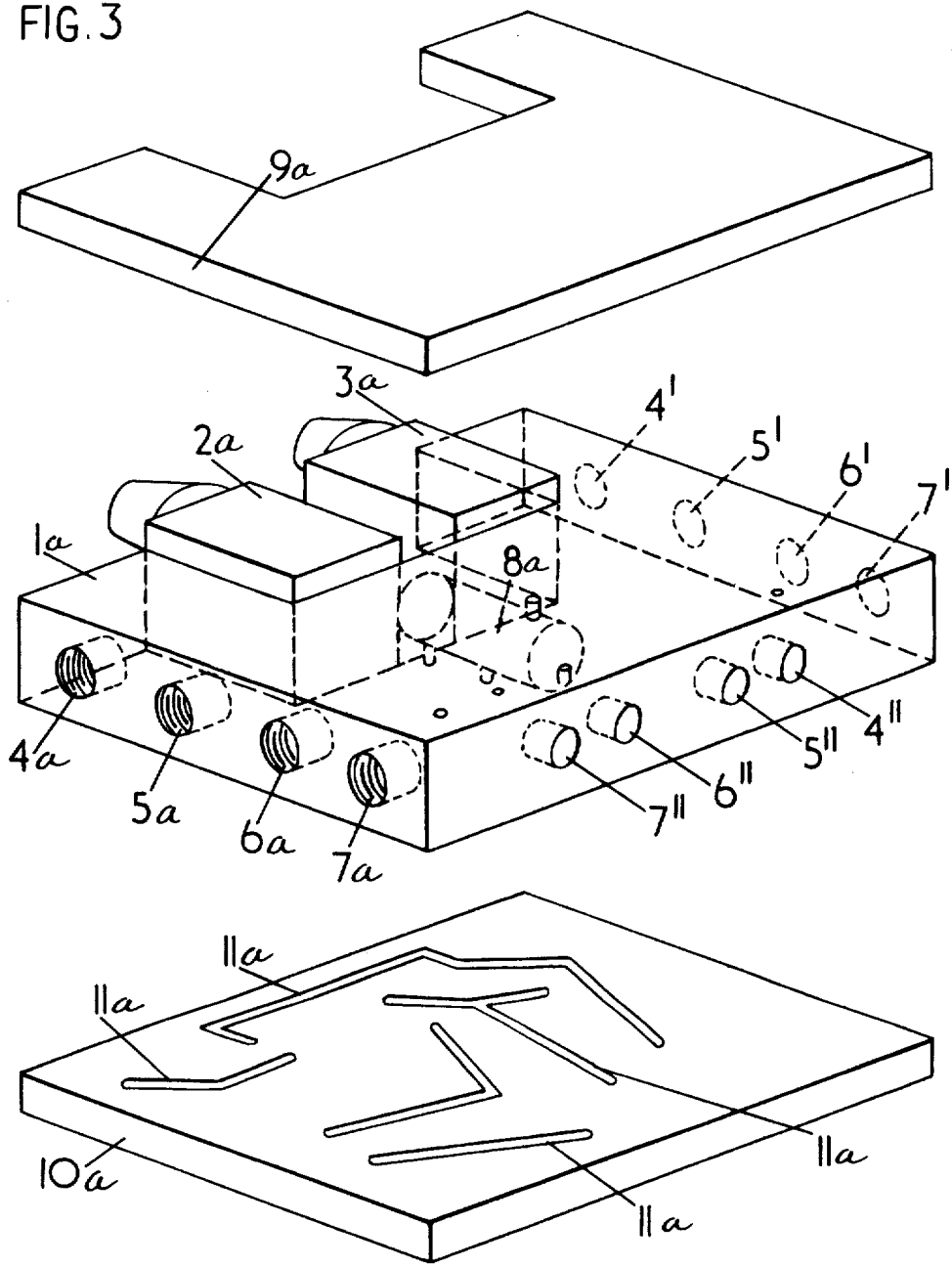
Figure 4:
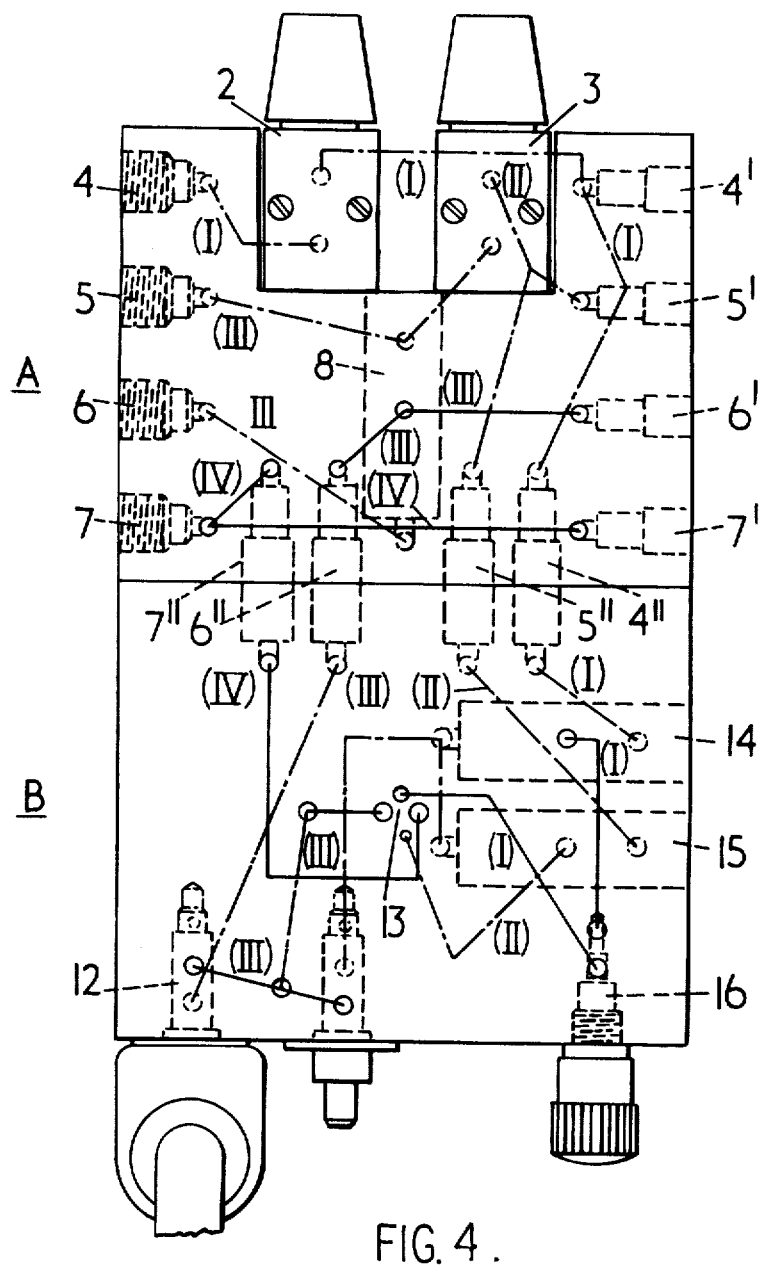

FIG. 3 is an exploded perspective view of a control manifold module for use in a dental unit in accordance with the invention (this control module is, essentially, a combination of units 8 and 10 shown in FIG. 1; and FIG. 4 is a diagrammatic plan view of a control module similar to that shown in FIG. 1 connected to an extension module incorporating controls for a dental turbine of the type requiring supplies of water, air at two pressures and exhaust services (i.e. an extension module similar to that shown at 18 in FIG. 1).

The body of the dental unit (not shown) incorporates supply conduits 1, 2, 3 and 4 (which may be of flexible piping) affording respectively supply water, low pressure air, high pressure air and exhaust services. An air mist lubrication unit 5 is desirably incorporated, in advance of a branch leading to a pedal control unit 6 which may incorporate a control valve 7 for one type of air driven dental handpiece.

The conduits 1 to 4 lead from the body of the unit to the lower part of an instrument table (not shown) which may be carried on an arm telescopically and rotationally movable relative to the body of the unit. Here the conduits terminate in a manifold 8 at self-sealing orifices 9 in which any desired pressure relief valves and relay valves may be incorporated. A modular joint 10 serving as an extension of the manifold has a mating configuration 11 serving to establish connection with the self-sealing supply orifices 9 when the joint 10 and the manifold 8 are brought together. The joint 10 presents what is in effect a duplicate of the self-sealing orifices 9, at 12 into operative connection with which an identically constructed modular joint 13 can be brought. In the same way, a further identically constructed modular joint 14 can be added on, optionally with a manifold end blank 15 so that the manifold 8 and the joints 10, 13 and 14 together assemble to form one long manifold.

Each of the joints 10, 13 and 14 presents a connection 16 into operative connection with which a modular manifold extension 17, 18 or 19 can be brought. Each connection 16 has the same pattern of self-sealing supply orifices 20, and each of the modular manifold extensions has the same pattern of orifice coupling members 21, but some of these latter, as indicated by the presence of shading, are "blind" whereby no connection to the respective self sealing supply orifice 20 is established.

Referring now to the module 17, which is intended for a dental handpiece sold under the Trade Name "WISPAIR" and incorporating a micro turbine, it will be seen that effective connection is made only with water and high pressure air. The latter may be such as to provide a maximum of 2 cubic feet of air per minute at eighty pounds per square inch. The module incorporates a weight responsive valve 22 in the air line serving also as a handpiece rest so that the air supply to the handpiece is not effectively established until the handpiece is lifted off the rest. The module also incorporates a relay valve 23 corporated by air from the conduit 3 when the valve 22 is opened, to establish a water connection from the conduit 1 to the handpiece only upon the opening of the valve 22. The water is conveyed through a conduit 24 by way of a control (needle) valve 25 to the handpiece (not shown) which may be served by way of a disconnectable joint 26. Provision may be made in this joint, if desired, for a low voltage electrical supply and/or a fibre light supply either or both of which may also be fed through the manifold 8 and the extension joints 10, 13 and 14.

Referring now to module 18, a weight responsive valve 27 is provided for a handpiece sold under the Trade Name "SYLVESTAIR" serving also as a rest for a handpiece so that high pressure air is fed to the handpiece connector 28 as soon as the handpiece is lifted off the rest. At the same time the valve feeds the high pressure air to a pair of relay valves 29, 30 serving to establish a connection for low pressure air and (low pressure) water respectively to the connector 28, the water being fed by way of the adjustable control valve 31. The connector 28 also has a connection to the exhaust conduit 4 which discharges by way of the already mentioned speed control valve 7.

The module 19 has a holder 32 for a dental spray and has effective connections only for the low pressure and water conduits 2 and 3 the other connections being "blind." The air-line passes by way of a non-return valve to the spray holder connector 33, whilst the waterline leads to the connector 33 by way of an adjustable control valve 34.

Although the manifold 8 and the disconnectable joint 10 have been shown as separate entities, it is not precluded to combine them into a single structure. That is to say, the connection with the self-sealing supply orifices 12 and the connection with the self-sealing supply orifices 20 may be provided on the manifold 8 instead on the separate extension joint 10.

Referring now to FIG. 3 of the drawings a control module for use in a dental unit according to the invention comprises a central block 1a having housings for water and air pressure regulators 2a and 3a, connections 4a, 5a, 6a and 7a for the supply of water, high pressure air, high pressure air and exhaust services, respectively and female elements 4', 4'', 5', 5'', 6', 6'', 7', 7'' of self-sealing coupling elements adapted to co-operate with corresponding elements in further extension modules. Central block 1a is also provided with a main control valve chamber 8a.

The module also comprises an upper plate 9a and a lower plate 10a and it will be seen that lower plate 10a has a plurality of grooves 11a cut therein. Similarly upper plate 9a has grooves in the lower surface thereof (not shown).

Referring now to FIG. 4 of the drawing the two elements thereof (namely the control module (A) similar to that shown in FIG. 1 and the extension control module (B) for supplying services to a particular dental handpiece requiring air at two pressures, water and exhaust services) each comprise an upper plate, a central block and a lower plate. The upper and lower plate are each provided with grooves in the respective surfaces thereof directed towards the central block and, in the drawing, grooves in the upper plate are shown as heavy lines and grooves in the lower plate as chain-dotted lines, with housings in the central block indicated in broken lines.

Each groove is labelled with the service it is designed to carry using the symbol I for water, II for low pressure air, III for high pressure air and IV for exhaust. The extension module (B) is similar to the module 18 shown in FIG. 1 and has a weight responsive valve 12 for its handpiece serving also as a rest for the handpiece so that high pressure air is fed to the handpiece connector 13 as soon as the handpiece is lifted off the rest. At the same time the valve feeds the high pressure air to a pair of relay valves 14 and 15 serving to establish a connection for low pressure air and (low pressure) water respectively to the connector 13, the water being fed by way of the adjustable control valve 16.

Although the module (A) has been shown with only one instrument control module (B) connected thereto at self-sealing coupling 4'', 5'', 6'' and 7'', it is not precluded to connect at self-sealing couplings 4', 5', 6' and 7' another instrument control module for another kind of type of dental instrument or, alternatively, to connect a linking module at 4', 5', 6' and 7' to which another instrument control module can be connected. In the same way, a further identically constructed linking module can be added to the first one, this second linking module also having connected thereto, an instrument control module.

This process can be repeated, within limits, so that the dentist can be supplied with a dental unit equipped with the appropriate number of linking and instrument control modules required to operate the range of instruments of his choice, the last manifold extension being supplied with an end blank.

Alternatively, the dentist may be supplied with a unit equipped only with module (A), to which is attached an end blank, and one instrument control module, so that the dentist can subsequently add to his instrumentation by connecting up one or more linking modules to which the appropriate number and type of instrument control modules can be attached.

Whilst the drawings have been described with reference to the particular modules shown, it will be understood that any desired range of manifold extension modules may be provided, connecting automatically to the appropriate service lines and containing whatever facilities and instrumentation might be desired for the particular instrument to be attached.

I claim:

1. A service supply system for supplying at least air and water to a dental instrument comprising a supply unit having air and water sources and respective air and water outlets a first coupling module having at least two first conduits extending therethrough from respective air and water inlets to an air and a water outlet, self-sealing coupling members at each end of said air and water conduits normally sealing the inlet and outlet ends of said conduits, a control module having at least two control conduits extending therethrough having dental instrument control means operatively connected to said conduits, said control module having self-sealing mating coupling members at the respective inlet ends of said control conduits disposed for simultaneous releasable connection to said self-sealing coupling members of said first coupling module and operable when connected to said self-sealing coupling members to establish fluid communication between said conduits in said coupling module and said control conduits, said self-sealing coupling members automatically sealing the respective ends of said conduits when disconnected from their mating coupling members.

2. A dental unit according to claim 1, wherein each coupling module comprises a central block member having housings for at least one set of coupling members in one outer face thereof adapted to mate with a corresponding set of female or male coupling elements in another coupling module, and housings for any valves or other controls for fluids passing through said module; an upper plate provided, in the surface thereof facing the central block, with a plurality of grooves; and a lower plate, provided in the surface thereof facing the central block with a plurality of grooves: the grooves in the said plates being connected with the housings in the central block via holes in the said central block to form the various conduits within the module.

3. The invention defined in claim 1 wherein said first coupling module is of block shaped configuration having a plurality of female self-sealing coupling members on one face of said module and a plurality of mating male self-sealing coupling members on the opposite face thereof aligned with said female coupling members and respectively connected thereto by second conduits communicating with the respective first conduit, whereby a plurality of said first coupling modules can be connected in series with each other, and a plurality of self-sealing coupling members on a face of said module intermediate said one and said opposite faces located to be connected to the mating self-sealing coupling members of said control module.

* * * * *